United States Patent [19]

Wiedemann et al.

[11] Patent Number: 4,479,962
[45] Date of Patent: Oct. 30, 1984

[54] INDAZOLOXYPROPANOLAMINE DERIVATIVES AND USE IN COMBATING, AND FOR THE PROPHYLAXIS OF, CARDIAC AND CIRCULATORY DISEASES

[75] Inventors: Fritz Wiedemann, Weinheim-Lützelsachsen; Helmut Michel, Mannheim; Wolfgang Weckerle, Grünstadt; Egon Roesch, Mannheim; Klaus Strein, Hemsbach, all of Fed. Rep. of Germany

[73] Assignee: Boehringer Mannheim GmbH, Mannheim, Fed. Rep. of Germany

[21] Appl. No.: 403,968

[22] Filed: Aug. 2, 1982

[30] Foreign Application Priority Data

Aug. 6, 1981 [DE] Fed. Rep. of Germany ....... 3131146

[51] Int. Cl.$^3$ ................. C07D 231/56; A61K 31/415
[52] U.S. Cl. ................................. 424/273 N; 548/371
[58] Field of Search .................... 424/273 N; 548/371

[56] References Cited

U.S. PATENT DOCUMENTS 4,143,149 3/1979 Wiedemann et al. ............... 548/371
4,216,314 8/1980 Raabe et al. ......................... 544/123

FOREIGN PATENT DOCUMENTS 2010261 6/1979 United Kingdom .

Primary Examiner—Henry R. Jiles
Assistant Examiner—Kurt G. Briscoe
Attorney, Agent, or Firm—Felfe & Lynch

[57] ABSTRACT

The present invention provides heteroaryloxypropanolamines and pharmaceutical compositions containing them, for combating, and for the prophylaxis of, cardiac and circulatory diseases. The heteroaryloxypropanolamines of the present invention are of the general formula:

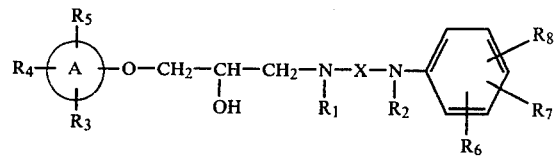

wherein A is a bi- or tricyclic heteroaromatic radical, which is optionally partly hydrogenated, X is a straight-chained or branched alkylene chain containing 2 to 6 carbon atoms, $R_1$ and $R_2$, which can be the same or different, are hydrogen atoms or lower alkyl or benzyl radicals, $R_3$, $R_4$ and $R_5$, which can be the same or different, are hydrogen atoms or lower alkyl, benzyl, formyl, lower alkanoyl, cyano, hydroxymethyl, lower alkoxycarbonyl or carbamoyl radicals or the divalent substituents sulfur or oxygen and $R_6$, $R_7$ and $R_8$, which can be the same or different, are hydrogen or halogen atoms, lower alkyl, nitro, amino, lower alkylthio or lower alkoxy radicals or $R_6$ and $R_7$ together represent an optionally unsaturated trimethylene chain; and the pharmacologically acceptable salts thereof.

The present invention also provides processes for the preparation of these compounds, as well as pharmaceutical compositions containing them.

32 Claims, No Drawings

INDAZOLOXYPROPANOLAMINE DERIVATIVES AND USE IN COMBATING, AND FOR THE PROPHYLAXIS OF, CARDIAC AND CIRCULATORY DISEASES

This invention relates to new heteroaryloxypropanolamine compounds and processes for their preparation. In an additional aspect the invention relates to pharmaceutical compositions for combating, and for the prophylaxis of, cardiac and circulatory diseases, containing such compounds.

In comparison with similar compounds, such as are disclosed in Federal Republic of Germany Patent Specifications Nos. 2,819,629 and 2,844,497, the new compounds according to the present invention display a surprising improved action.

Thus, according to the present invention, there are provided new heteroaryloxypropanolamines of the general formula:

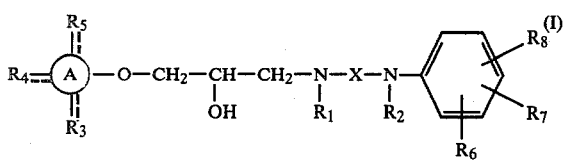

wherein A is a bi- or tricyclic heteroaromatic radical which is optionally partly hydrogenated, X is a straight-chained or branched alkylene chain containing 2 to 6 carbon atoms, $R_1$ and $R_2$, which can be the same or different, are hydrogen atoms or lower alkyl or benzyl radicals, $R_3$, $R_4$ and $R_5$, which can be the same or different, are hydrogen atoms or lower alkyl, benzyl, formyl, lower alkanoyl, cyano, hydroxymethyl, lower alkoxycarbonyl or carbamoyl radicals or the divalent substituents sulphur or oxygen and $R_6$, $R_7$ and $R_8$, which can be the same or different, are hydrogen or halogen atoms, lower alkyl, nitro, amino, lower alkylthio or lower alkoxy radicals or $R_6$ and $R_7$ together represent an optionally unsaturated trimethylene chain; as well as the pharmacologically acceptable salts thereof.

Since the compounds of general formula (I) possess asymmetrical carbon atoms, the present invention also includes the optically-active forms and racemic mixtures of these compounds.

Within the meaning of the present invention, in general formula (I) the bi- and tricyclic heteroaromatic radicals A can be, for example, indole, indolizine, isoindole, benzotriazole, indazole, purine, quinazoline, benzthiadiazole, cinnoline, carboline, carbazole, acridine, phenazine or cinnoline, carboline, carbazole, acridine, phenazine or benzimidazole and preferably indole, benzimidazole, indazole, benzotriazole or carbazole; or partly hydrogenated heteroaromatic radicals, for example indoline, isoindoline, pyrroline or imidazoline and preferably indoline.

The broken lines joining the substituents $R_3$, $R_4$ and $R_5$ to the ring A in general formulae (I), (II), (IV) and (VI) are intended to indicate a second bond when $R_3$, $R_4$ and/or $R_5$ represent the divalent substituent sulphur or oxygen.

The lower alkyl radicals in the definitions of $R_1$, $R_2$, $R_3$, $R_4$, $R_5$, $R_6$, $R_7$ and $R_8$ and the lower alkyl moieties in lower alkanoyl, lower alkoxycarbonyl, lower alkoxy and lower alkylthio are straight-chained or branched radicals containing up to 6 and preferably up to 4 carbon atoms, for example methyl, ethyl, n-propyl, isopropyl, n-butyl, isobutyl, sec.-butyl, tert.-butyl, n-pentyl and n-hexyl radicals, methyl and ethyl radicals being especially preferred.

The alkylene chain represented by the substituent X is a straight-chained or branched chain containing 2 to 6 and preferably 2 to 4 carbon atoms, the ethylene and trimethylene radicals being especially preferred.

Halogen in the scope of the present invention is to be understood to mean fluorine, chlorine, bromine or iodine, fluorine, chlorine and bromine being preferred.

The present invention also provides processes for the preparation of compounds of general formula (I). The compounds can be obtained in known manner, for example by:

(a) reacting a compound of the general formula:

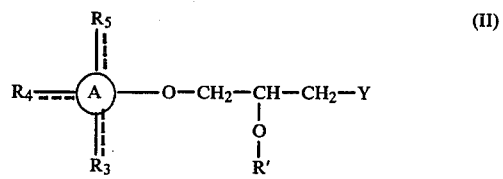

in which A, $R_3$, $R_4$ and $R_5$ have the same meanings as above, R' is a hydrogen atom or a protective group and Y is a reactive group or R' and Y together represent a valency bond, with a compound of the general formula:

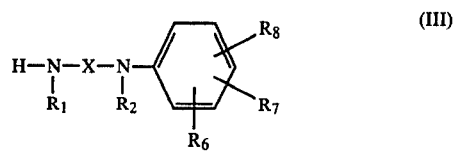

in which X, $R_1$, $R_2$, $R_6$, $R_7$ and $R_8$ have the same meanings as above, whereafter a protective group R' when present is split off by hydrolysis or hydrogenolysis; or (b) reacting a compound of the general formula:

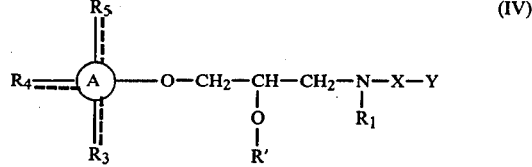

in which A, $R_3$, $R_4$, $R_5$, $R_1$ and X have the same meanings as above, R' is a hydrogen atom or a protective group and Y is a reactive group, with a compound of the general formula:

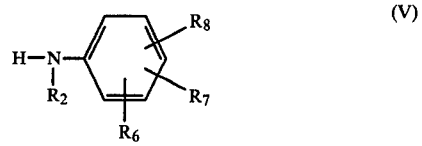

in which $R_2$, $R_6$, $R_7$ and $R_8$ have the same meanings as above, whereafter, when a protective group R' is present, it is subsequently split off; or (c) when, in general formula (I), $R_1$ is a hydrogen atom and X is an ethylene or propylene radical, reacting a compound of the general formula:

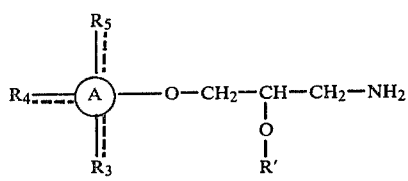

in which A, $R_3$, $R_4$ and $R_5$ have the same meanings as above and R' is a protective group, with an aldehyde of the general formula:

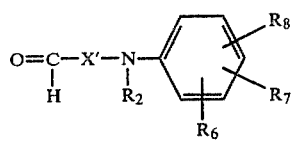

in which $R_2$, $R_6$, $R_7$ and $R_8$ have the same meanings as above and X' is a methylene or ethylene radical; whereafter the Schiff base thereby formed is reduced and the protective group R' is split off; or (d) reducing a compound of the general formula:

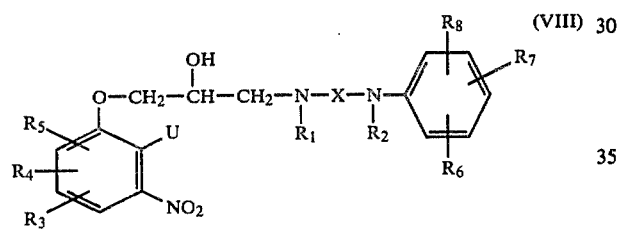

in which $R_1$, $R_2$, $R_3$, $R_4$, $R_5$, $R_6$, $R_7$, $R_8$ and X have the same meanings as above and U is a nitro group, an alkylamino radical, or an alkoxycarbonylmethyl radical, whereby the intermediate formed is converted into a compound of general formula (I) under acid conditions or by reacting with acetylenedicarboxylic acid, nitrous acid or an organic ester of nitrous acid, formic acid or acetic acid or a carbonic acid derivative; and subsequently, if desired, converting a compound obtained of general formula (I) into a different compound of general formula (I) and, if desired, converting a compound obtained of general formula (I) into a pharmacologically acceptable salt thereof.

The reaction according to process (a) is, as a rule, carried out without the use of a solvent by melting the reaction components and subsequently reacting at ambient temperature. However, it is also possible to carry out the reaction in a solvent, for example dimethylformamide or an alcohol, such as ethanol or a glycol ether. The reaction temperature is then from 20° to 80° C.

The reaction according to process (b) is carried out under the conditions generally well known for alkylations. The reactive group in compounds of general formula (IV) is preferably a halogen atom or a sulphonic acid ester group. As a rule, the alkylation is carried out in a polar solvent, for example dimethylformamide or dimethyl sulfoxide.

The reaction of an amine of general formula (VI) with an aldehyde of general formula (VII) with the splitting off of water is usually carried out in toluene as solvent, by acid catalysis, p-toluenesulphonic acid preferably being used. The water formed by the reaction is distilled off azetropically. The reduction of the Schiff base to give a compound of general formula (I) is, as a rule, carried out by catalytical hydrogenation in the presence of a noble metal catalyst, for example palladium or platinum. However, the reduction can also be carried out with a complex hydride, for example lithium aluminium hydride.

The compounds of general formula (VIII) used in process (d) are prepared under the same reaction conditions as described in the case of process (a). The intermediate products thus obtained are then reduced by catalytic hydrogenation. In this case, it is especially preferred to use noble metal catalysts, for example palladium or platinum. If the compound of general formula (I) is a quinoxaline derivative, the corresponding phenylenediamine is reacted with acetylenedicarboxylic acid in water at a temperature of from 40° to 100° C. The resultant isomers are separated by fractional crystallisation or by column chromatography on silica gel. If the compound of general formula (I) is a benzotriazole compound, the corresponding phenylenediamine derivative is reacted with sodium nitrite in aqueous acetic acid at a temperature of from 0° to 30° C. However, the reaction can also be carried out with a lower alkyl nitrous acid ester in an organic solvent. If the compound of general formula (I) is a benzimidazole derivative, the corresponding phenylenediamine is reacted with formic acid or acetic acid. As a rule, the reaction is carried out under reflux conditions. If the compound of general formula (I) is a benzimidazolinone derivative, the corresponding phenylenediamine derivative is reacted with a carbonic acid derivative, for example diethyl carbonate, diphenyl carbonate, urea or phosgene. As solvent there can be used, for example, dimethylformamide, toluene or also water, at a temperature of from 20° to 110° C. If the compound of general formula (I) is an indole derivative, the hydrogenation of the corresponding compound of general formula (VIII) is carried out under acidic conditions, for example in the presence of acetic acid, a ring closure to give the desired indole derivative thereby taking place simultaneously.

The possibly necessary splitting off of protective groups can be carried out by conventional methods. A benzyl protective group is split off by hydrogenation in the presence of a noble metal catalyst, for example palladium or platinum. A tetrahydropyranyl or acyl protective group is split off under acidic conditions. For this purpose, there can be used, for example, mineral acids, such as hydrochloric acid or sulfuric acid, or also Lewis acids, for example boron trifluoride.

A subsequent conversion of a compound of general formula (I) into another compound of general formula (I) can be, for example, the reduction of a nitro group to give an amino group or of a carboxylic acid ester radical to give a hydroxymethyl radical. The reduction can be carried out by generally known methods, for example by catalytic hydrogenation in the presence of a noble metal catalyst, such as palladium or platinum, or with a complex metal hydride, such as lithium aluminium hydride, in an aprotic solvent, such as diethyl ether or tetrahydrofuran.

The compounds of general formula (I) according to the present invention can be obtained in the form of a racemic mixture. The separation of the racemate into the optically-active forms is carried out by known methods via the diastereometric salts of an optically-active acid, for example tartaric acid, malic acid or camphorsulphonic acid.

The new compounds of general formula (I) are, under the reaction conditions of the above-described processes, preponderantly obtained as acid-addition salts, for example as hydrochlorides, but can readily be converted into the corresponding free bases by means of known methods.

For the conversion of compounds of general formula (I) into their pharmacologically acceptable salts, they are preferably reacted in an organic solvent with an equivalent amount of an inorganic or organic acid, for example hydrochloric acid, hydrobromic acid, phosphoric acid, sulfuric acid, acetic acid, citric acid or maleic acid.

For the preparation of pharmaceutical compositions, the compounds of general formula (I) are mixed in the usual manner with appropriate pharmaceutical carrier substances, aroma, flavouring and colouring materials and shaped, for example, into tablets or dragees or, with the addition of appropriate adjuvants, are suspended in water or an oil, for example olive oil.

The new compounds of general formula (I) according to the present invention and the salts thereof can be administered enterally or parenterally in liquid or solid form. As injection medium it is preferred to use water which contains the additives usual in the case of injection solutions, such as stabilizing agents, solubilising agents or buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and/or sweetening agents.

The dosage to be used in the case of humans depends upon the age, weight and general state of health of the patient, the severity of the disease, the nature of simultaneously administered other treatment, the frequency of administration and the nature of the intended effect. In general, the daily dosage of the active compound is from 0.1 to 50 mg. per kg. of body weight. Normally, 0.5 to 40 mg. and preferably 1.0 to 20 mg./kg. body weight/day in one or more individual doses suffice in order to achieve the desired improvement.

Preferred compounds according to the present invention are, apart from those mentioned in the specific Examples, also the following compounds:

1-(6-hydroxymethylindol-4-yloxy)-3-[2-(2,6-dimethylphenylamino)-ethylamino]-propan-2-ol 1-(6-methoxycarbonylindol-4-yloxy)-3-[2-(2,6-dimethylphenylamino)-ethylamino]-propan-2-ol 1-(2-cyanoindol-4-yloxy)-3-[2-(2,6-dimethylphenylamino)ethylamino]-propan-2-ol 1-(indazol-4-yloxy)-3-[2-(2,6-dichlorophenylamino)ethylamino]-propan-2-ol 1-(indazol-7-yloxy)-3-[2-(2,6-dimethylphenylamino)ethylamino]-propan-2-ol 1-(6-methylindazol-4-yloxy)-3-[2-(2,6-dimethylphenylamino)-ethylamino]-propan-2-ol 1-(2-methylbenzimidazol-4-yloxy)-3-[2-(2,6-dimethylphenylamino)-ethylamino]-propan-2-ol 1-(7-methylbenzimidazol-4-yloxy)-3-[2-(2,6-dimethylphenylamino)-ethylamino]-propan-2-ol 1-(1,3-dimethylbenzimidazolin-2-on-4-yloxy)-3-[2-(2,6-dimethylphenylamino)-ethylamino]-propan-2-ol 1-(7-methylbenzotriazol-4-yloxy)-3-[2-(2,6-dimethylphenylamino)-ethylamino]-propan-2-ol The following Examples are given for the purpose of illustrating the present invention:

EXAMPLE 1

1-(Indazol-4-yloxy)-3-[2-(2,6-dimethylphenylamino)ethylamino]-propan-2-ol 6.8 g. 1-(2-Benzylindazol-4-yloxy)-3-[2-(2,6-dimethylphenylamino)-ethylamino]-propan-2-ol in 100 ml. methanol and 10 ml. concentrated hydrochloric acid are hydrogenated over 0.9 g. of 10% palladium-charcoal. After suction filtration, the filtrate is evaporated, the residue is dissolved in water, rendered alkaline with aqueous sodium hydroxide solution and extracted with methylene chloride. The organic phase is evaporated and the residue is triturated with diethyl ether and filtered off with suction. After recrystallization from ethyl acetate, the desired compound is obtained in a yield of 3.9 g. (72% of theory); m.p. 127°–128° C.

The 1-(2-benzylindazol-4-yloxy)-3-[2-(2,6-dimethylphenylamino)-ethylamino]-propan-2-ol used as starting material is prepared in the following manner:

6.2 g. 2-Benzyl-4-(2,3-epoxypropoxy)-indazole and 7.2 g. 2-(2,6-dimethylphenylamino)-ethylamine are stirred for 20 hours at 70° C. The reaction mixture is then dissolved in methylene chloride and purified chromatographically over a silica gel column using methylene chloride/methanol (saturated with ammonia) (20:1 v/v) as elution agent. After evaporation, the desired compound is obtained in the form of a viscous oil in a yield of 6.8 g. (69% of theory).

EXAMPLE 1a

In a manner analogous to that described in Example 1, there is obtained 1-(indazol-4-yloxy)-3-[N-methyl-2-(2,6-dimethylphenylamino)-ethylamino]-propan-2-ol in a yield of 39% of theory in the form of colourless crystals; m.p. 120°–121° C. (recrystallized from propan-2-ol) from 1-(2-benzylindazol-4-yloxy)-3-[N-methyl-2-(2,6-dimethylphenylamino)-ethylamino]-propan-2-ol by hydrogenolysis of the benzyl group.

The starting material used is obtained from 2-benzyl-4-(2,3-epoxypropoxy)-indazole by reaction with N-methyl-2-(2,6-dimethylphenylamino)-ethylamine (b.p.$_{0.05}$ 93°–95° C.; benzoate m.p. 145°–146° C.) for 22 hours at 70° C. The desired compound is obtained in a yield of 76% of theory in the form of a brownish oil.

EXAMPLE 1b

In a manner analogous to that described in Example 1, there is obtained 1-(carbazol-4-yloxy)-3-[2-(2,6-dimethylphenylamino)-ethylamino]-propan-2-ol in a yield of 52% of theory (benzoate: colourless crystals; m.p. 162°–163° C. (after recrystallization from ethyl acetate)) by the reaction of 4-(2,3-epoxypropoxy)-carbazole with 2-(2,6-dimethylphenylamino)-ethylamine.

EXAMPLE 2

1-(Indol-4-yloxy)-3-[2-(2,6-dimethylphenylamino)-ethylamino]-propan-2-ol dihydrogen carbonate 4.7 g. 1-(Indol-4-yloxy)-2,3-epoxypropane are dissolved in 100 ml. methanol and 8.2 g. 2-(2,6-dimethylphenylamino)-ethylamine and left to stand for 4 days at ambient temperature. After removal of the solvent, the residue is taken up in water and ethyl acetate, mixed with carbon dioxide and the crystals obtained are filtered off with suction. After drying, there are obtained 5.0 g. of the desired compound (50% of theory); m.p. 99°–110° C.

The following compounds are obtained in a manner analogous to that described in Example 2:

|   | yield % | m.p. °C. (solvent) |
|---|---|---|
| (a) 1-(oxindol-4-yloxy)-3-[2-(2,6-dimethylphenylamino)-ethylamino]-propan-2-ol benzoate from 1-(oxindol-4-yloxy)-2,3-epoxypropane and 2-(2,6-dimethylphenylamino)-ethylamine | 11 | 190 (propan-2-ol) |
| (b) 1-(6-methylindol-4-yloxy)-3-[2-(2,6-dimethylphenyl-amino)-ethylamino]-propan-2-ol benzoate from 1-(6-methylindol-4-yloxy)-2,3-epoxypropane and 2-(2,6-dimethylphenylamino)-ethyl-amine | 15 | 97–99 (ethyl acetate/ligroin) |
| (c) 1-(2-ethoxycarbonylindol-4-yloxy)-3-[2-(2,6-dimethyl-phenylamino)-ethylamino]-propan-2-ol from 1-(2-ethoxycarbonylindol-4-yloxy)-2,3-epoxypropane and 2-(2,6-dimethylphenylamino)-ethylamine | 42 | 121–123 (ethyl acetate) |
| (d) 1-(3-cyanoindol-4-yloxy)-3-[2-(2,6-dimethylphenylamino)-ethylamino]-propan-2-ol benzoate from 1-(3-cyanoindol-4-yloxy)-2,3-epoxypropane and 2-(2,6-dimethylphenylamino)-ethyl-amine | 41 | 150–152 (ethyl acetate) |
| (e) 1-(1-formylindolin-4-yloxy)-3-[2-(2,6-dimethylphenyl-amino)-ethylamino]-propan-2-ol from 1-(1-formylindolin-4-yloxy)-2,3-epoxypropane and 2-(2,6-dimethylphenylamino)-ethyl-amine | 27 | 110–112 (ethyl acetate) |

EXAMPLE 3

1-(2-Hydroxymethylindol-4-yloxy)-3-[2-(2,6-dimethylphenylamino)-ethylamino]-propan-2-ol cyclamate A solution of 2.7 g. 1-(2-ethoxycarbonylindol-4-yloxy)-3-[2-(2,6-dimethylphenylamino)-ethylamino]-propan-2-ol (see Example 2c) in 25 ml. anhydrous tetrahydrofuran is added dropwise to a suspension of 1.2 g. lithium aluminium hydride in 50 ml. anhydrous tetrahydrofuran. The reaction mixture is then stirred for 3 hours at ambient temperature, mixed, while cooling, with an aqueous solution of sodium chloride, filtered and the filtrate evaporated in a vacuum. The crude base obtained is dissolved in propan-2-ol, mixed with the calculated amount of N-cyclohexylsulfaminic acid and the precipitated salt filtered off with suction. After recrystallization from methanol/ethyl acetate, there is obtained 1.5 g. (42% of theory) of the desired compound: m.p. 98° C.

EXAMPLE 4

1-(Oxindol-4-yloxy)-3-[2-(2,6-dimethylphenylamino)-ethylamino]-propan-2-ol benzoate 11.3 g. Ethyl [2-(2,3-epoxypropoxy)-6-nitrophenyl]-acetate (see Federal Republic of Germany Patent Specification No. 29 058 762) and 13.1 g 2-(2,6-dimethylphenylamino)-ethylamine (0.08 mol) in 100 ml. methanol are left to stand for 2 days at ambient temperature. 100 ml. Acetic acid and 1 g. 10% palladium-charcoal are then added thereto, followed by hydrogenation at a hydrogen pressure of 1 bar. After filtering off the catalyst, the filtrate is distilled in a vacuum and the residue remaining behind is dissolved in water. The base is precipitated out by adding an aqueous solution of potassium carbonate and extracted with ethyl acetate. After drying the extract over anhydrous sodium sulfate and evaporating the organic phase, there are obtained 7.2 g. of crude product. By dissolving this in propan-2-ol and adding the calculated amount of benzoic acid, there are obtained 4.3 g. (21% of theory) of the desired compound; m.p. 191° C.

EXAMPLE 5

1-(Benzimidazol-4-yloxy)-3-[2-(2,6-dimethylphenylamino)-ethylamino]-propan-2-ol dihydrochloride A solution of 21.5 g. 2,3-diamino-1-{2-hydroxy-3-[2-(2,6-dimethylphenylamino)-ethylamino]-propoxy}-benzene trihydrochloride in 150 ml. formic acid is boiled under reflux for 6 hours. After evaporating the reaction mixture in a vacuum, the residue obtained is taken up in 200 ml. 2N hydrochloric acid, boiled under reflux for 4 hours, mixed with active charcoal and filtered while hot. The filtrate is evaporated to dryness and the residue then recrystallized. There are obtained 3.5 g. (17.4% of theory) of the desired compound: m.p. 128°–131° C.

EXAMPLE 6

1-(3-Methylbenzimidazol-4-yloxy)-3-[2-(2,6-dimethylphenylamino)-ethylamino]-propan-2-ol dihydrochloride In a manner analogous to the preceding Example, by reacting 3-amino-2-methylamino-1-(2-hydroxy-3-[2-(2,6-dimethylphenylamino)-ethylamino]-propoxy)-benzene trihydrochloride with formic acid, there are obtained 2.1 g. (14% of theory) of the desired compound; m.p. 94°–96° C. (after recrystallization from ethanol/diethyl ether).

EXAMPLE 7

1-(Benzimidazolin-4-yloxy)-3-[2-(2,6-dimethylphenylamino)-ethylamino]-propan-2-ol hydrochloride Phosgene is passed into a solution of 21.5 g. 2,3-diamino-1-{2-hydroxy-3-[2-(2,6-dimethylphenylamino)-ethylamino]-propoxy}-benzene trihydrochloride in 400 ml. water for 45 minutes, while cooling (internal temperature 20° to 25° C.). After flushing with nitrogen, the aqueous supernatant is decanted off and the precipitate recrystallized from ethanol/methanol (1:1 v/v), with the addition of active charcoal. There are obtained 6.6 g. (35% of theory) of the desired compound; m.p. 248°-250° C.

The following compounds are obtained in an analogous manner from the appropriately substituted phenylene-diamines and phosgene:

|     | | yield % | m.p. °C. (solvent) |
| --- | --- | --- | --- |
| (a) | 1-(3-methylbenzimidazolinon-4-yloxy)-3-[2-(2,6-dimethyl-phenylamino)-ethylamino]-propan-2-ol from 3-amino-2-methylamino-1-(2-hydroxy-3-[2-(2,6-dimethyl-phenylamino)-ethylamino]-propoxy)-benzene trihydrochloride | 11 | 179–180 (methanol) |
| (b) | 1-(7-methylbenzimidazolinon-4-yloxy)-3-[2-(2,6-dimethyl-phenylamino)-ethylamino]-propan-2-ol dihydrochloride from 2,3-diamino-1-(2-hydroxy-3-[2-(2,6-dimethylphenylamino)-ethylamino]-propoxy)-4-methyl-benzene tetrahydrochloride | 19 | 240–242 (methanol) |

EXAMPLE 8

1-(Benztriazol-4-yloxy)-3-[2-(2,6-dimethyl-phenylamino)-ethylamino]-propan-2-ol dihydrochloride 1.38 g. Sodium nitrite dissolved in 2.2 ml. water are added to a solution, cooled to 0° C., of 9.1 g. 2,3-diamino-1-{2-hydroxy-3-[2-(2,6-dimethylphenylamino)-ethylamino]-propoxy}-benzene trihydrochloride in 12 ml. water and 4.6 ml. glacial acetic acid. After stirring for 2 hours at ambient temperature, the reaction mixture is evaporated to dryness, the residue is taken up in chloroform and the solution is washed with 1M hydrochloric acid and water, dried and evaporated. The residue is recrystallized from ethanol-ethyl acetate, with the addition of active charcoal, to give 2.2 g. (26% of theory) of the desired compound; m.p. 230°-232° C.

EXAMPLE 9

1-(3-Methyl-2-quinoxalinon-5-yloxy)-3-[2-(2,6-dimethylphenylamino)-ethylamino]-propan-2-ol dihydrochloride and 1-(3-methyl-2-quinoxalinon-8-yloxy)-3-[2-(2,6-dimethylphenylamino)-ethylamino]-propan-2-ol dihydrochloride A solution of 11.4 g. acetylenedicarboxylic acid in 125 ml. water is added to a hot solution of 45.4 g. 2,3-diamino-1-(2-hydroxy-3-[2-(2,6-dimethylphenylamino)-ethylamino]-propoxy)-benzene trihydrochloride in 150 ml. water. After standing overnight at ambient temperature the precipitate obtained is filtered off with suction and the isomers separated by fractional crystallization from ethanol. There are obtained 1.6 g. (6.8% of theory) of the 5-substituted quinoxalinone (m.p. 145°-148° C.) and 1.08 g. (4.6% of theory) of the 8-substituted quinoxalin-one (m.p. 180°-183° C.).

The diamines used as starting material for the preparation of the above compounds are obtained in the following manner:

25.4 g. N-Benzyl-2-(2,6-dimethylphenylamino)-ethylamine and 24.2 g. 2,3-dinitro-1-(2,3-epoxypropoxy)-benzene are boiled under reflux for 4 hours in 300 ml. ethanol. The reaction solution is then diluted with 300 ml. ethanol and hydrogenated at 50° C. and 30 bar hydrogen pressure in the presence of 7 g. 10% palladium-active charcoal. The catalyst is then filtered off, the filtrate is acidified with 2N hydrochloric acid and, after evaporation, there is obtained the amorphous 2,3-diamino-1-{2-hydroxy-3-[2-(2,6-dimethylphenylamino)-ethylamino]-propoxy}-benzene trihydrochloride, which is used as a preliminary stage for the syntheses according to Examples 5, 7, 8 and 9.

In an analogous manner, there is obtained 3-amino-2-methylamino-1-{2-hydroxy-3-[2-(2,6-dimethylphenylamino)-ethylamino]-propoxy}-benzene trihydrochloride, which is used as starting material for the syntheses according to Examples 6 and 7a but, prior to the hydrogenation as in the preceding Example, the o-nitro group is replaced by a methylamino radical by reacting with a 40% aqueous methylamine solution for 2 hours at 60° C.; as well as 2,3-diamino-1-{2-hydroxy-3-[2-(2,6-dimethylphenylamimo)-ethylamino]-propoxy}-4-methylbenzene tetrahydrochloride as a preliminary stage for the synthesis according to Example 7b from 2,3-dinitro-1-(2,3-epoxypropoxy)-4-methylbenzene and N-benzyl-2-(2,6-dimethylphenylamino)-ethylamine.

EXAMPLE 10

In a manner analogous to that described in Example 1, from 2-benzyl-4-(2,3-epoxypropoxy)-indazole and the appropriate, correspondingly substituted 2-(phenylamino)-ethylamine and subsequent hydrogenolytic splitting off of the benzyl protective group, there are obtained the following compounds:

|     | | yield % | m.p. °C. 13 |
| --- | --- | --- | --- |
| (a) | 1-(indazol-4-yloxy)-3-[2-(phenylamino)-ethylamino]-propan-2-ol from 2-(phenylamino)-ethylamine | 53 | 134–135 (ethyl acetate) |
| (b) | 1-(indazol-4-yloxy)-3-[2-(4-methoxyphenylamino)-ethylamino]-propan-2-ol oxalate from 2-(4-methoxyphenylamino)-ethylamine | 7 | 163–166 (aqueous ethanol) |
| (c) | 1-(indazol-4-yloxy)-3-[2-(3-aminophenylamino)-ethyl-amino]-propan-2-ol from 2-(3-aminophenylamino)-ethylamine | 43 | 129–132 (propan-2-ol) |
| (d) | 1-(indazol-4-yloxy)-3-[2-(2-methylphenylamino)-ethyl amino]-propan-2-ol from 2-(2-methylphenylamino)-ethylamine | 44 | 131–132 (aqueous ethanol) |
| (e) | 1-(indazol-4-yloxy)-3-[2-(indanyl-4-amino)-ethyl amino]-propan-2-ol from 2-(indanyl-4-amino)-ethyl-amine | 53 | 120–121 (ethyl acetate) |
| (f) | 1-(indazol-4-yloxy)-3-[3-2,6-dimethylphenylamino)-propylamino]-propan-2-ol from 3-(2,6-dimethylphenylamino)-propylamine | 54 | 160–162 (ethyl acetate) |

-continued

|   | yield % | m.p. °C. |
|---|---|---|
| (g) 1-(indazol-5-yloxy)-3-[2-(2,6-dimethylphenylamino)-ethylamino]-propan-2-ol hydrogen fumarate from 2-benzyl-5-(2,3-epoxypropoxy)-indazole and 2-(2,6-dimethylphenylamino)-ethylamine | 48 | 168–169 (ethanol) |
| (h) 1-(7-methylindazol-4-yloxy)-3-[2-(2,6-dimethylphenyl-amino)-ethylamino]-propan-2-ol hydrogen fumarate from 2-benzyl-4-(2,3-epoxypropoxy)-7-methylindazole and 2-(2,6-dimethylphenylamino)-ethyl-amine | 53 | 182–184 (ethanol) |

EXAMPLE 11

The following compounds are obtained in a manner analogous to that described in Example 1:

|   | yield % | m.p. °C. (solvent) |
|---|---|---|
| (a) 1-(2-methylindazol-4-yloxy)-3-[2-(2,6-dimethylphenyl-amino)-ethylamino]-propan-2-ol fumarate from 4-(2,3-epoxypropoxy)-2-methyl-indazole and 2-(2,6-dimethyl-phenylamino)-ethylamine | 16 | 186–187 (ethanol) |
| (b) 1-(3-methylbenztriazol-4-yloxy)-3-[2-(2,6-dimethyl-phenylamino)-ethylamino]-propan-2-ol hydrochloride from 4-(2,3-epoxypropoxy)-3-methyl-benztriazole and 2-(2,6-dimethylphenylamino)-ethylamine | 14 | 118–120 (ethanol) |
| (c) 1-(2,1,3-benzthiadiazol-4-yloxy)-3-[2-(2,6-dimethyl-phenylamino)-ethylamino]-propan-2-ol from 4-(2,3-epoxypropoxy)-benz-2,1,3-thiadiazole and 2-(2,6-dimethylphenylamino)-ethylamine | 29 | 102–104 (diethyl ether) |

EXAMPLE 12

1-(Indazol-4-yloxy)-3-[2-(2-chlorophenylamino)-ethylamino]-propan-2-ol 7.8 g. (175 mmol) 1-[1-(Tetrahydropyran-2-yl)-indazol-4-yloxy]-3-[2-(2-chlorophenylamino)-ethylamino]-propan-2-ol in 250 ml. ethanol are mixed with the ion exchanger "Amberlite" CG 120 II (H+ form) and then stirred for 24 hours at 25° C. The ion exchanger is separated off and thoroughly washed with 2% ammonia in methanol. The combined solutions are evaporated and the residue obtained is recrystallized from ethyl acetate. There are obtained 3.6 g. (57% of theory) of the desired compound; m.p. 129°–130° C.

The starting material used in the above Example is obtained in the following manner:

5.5 g. (20 mmol) 4-(2,3-Epoxypropoxy)-1-(2-tetrahydropyranyl)-indazole and 6.8 g. (40 mmol) 2-(2-chlorophenylamino)-ethylamine are intimately mixed with gentle warming and then left to stand for 24 hours at 25° C. After chromatography on silica gel, using ethyl acetate-methanol-triethylamine (100:10:1 v/v/v) as elution agent, followed by evaporation of the appropriate fractions, there is obtained the desired addition product in the form of a colourless, viscous oil. The yield is 7.8 g. (88% of theory).

In an analogous manner, from 4-(2,3-epoxypropoxy)-1-(2-tetrahydropyranyl)-indazole and the appropriately substituted phenyldiamines and subsequent splitting off of the protective group, there are obtained the following compounds:

|   | yield % | m.p. °C. (solvent) |
|---|---|---|
| (a) 1-(indazol-4-yloxy)-3-[2-(2-methylthiophenylamino)-ethylamino]-propan-2-ol fumarate from 2-(2-methylthiophenylamino)-ethylamine | 61 | 140–141 (ethanol/ ethyl acetate) |
| (b) 1-(indazol-4-yloxy)-3-[2-(3-nitrophenylamino)-ethyl-amino]-propan-2-ol from 2-(3-nitrophenylamino)-ethylamine | 57 | 148–150 (ethyl acetate) |
| (c) 1-(indazol-4-yloxy)-3-[2-(4-chloro-2-methoxyphenylamino)-ethylamino]-propan-2-ol from 2-(4-chloro-2-methoxyphenyl-amino)-ethylamine | 65 | 145–146 (ethyl acetate) |

EXAMPLE 13

Tablets containing 10 mg. of 1-(indazol-4-yloxy)-3-[2-(2,6-dimethylphenyl)-amino)-ethylamino]-propan-2-ol are prepared according to the following formulation:

1-(indazol-4-yloxy)-3-[2-(2,6-dimethylphenylamino)-ethylamino]-propan-2-ol: 10 g.
lactose: 80 g.
starch: 29 g.
magnesium stearate: 1 g.

The above-mentioned active compound is finely pulverized and mixed with the lactose and starch. The mixture obtained is then granulated in conventional manner. Magnesium stearate is added to the granulate and the mixture obtained then pressed to give 1000 tablets, each with a weight of 0.12 g.

The following tests were carried out to determine the effectiveness of the compounds of the invention in combating and for the prophylaxis of cardiac and circulatory diseases.

Cardiotonic Effect

For the tests, mongrel dogs of both sexes were used. In a preparatory operation, catheters had been inserted under aseptic conditions into the Arteria and *Vena femoralis* and, through the myocardium, into the left ventricle. The tests were begun not less than ten days after this operation, when the animals were again in a clinically healthy state.

Throughout the test, during which the animals were wake, the arterial blood pressure was determined by means of a catheter and an electromechanical transducer. In addition, the pressure in the left ventricle was continuously measured by means of a tip manometer which had been introduced into the ventrical catheter and advanced as far as the heart, and from that pressure the differentiation based on the time dp/dt max was determined. The heart rate (f cor) was computed by counting the heart beats at a fast chart speed at given times of measurement.

At the beginning of the experiments the animals were injected intravenously with 0.3 µg/kg of isoprenalin and the effect on the rapidity of the pressure increase recorded. After dissipation of this injection the test compounds were injected intravenously in increasing dosage rates in intervals of ten minutes and again the effect of each dosage level determined.

For the characterization of the effectiveness of the test compounds two criteria were calculated:

1. The termination of the achievable maximum effect in comparison to isoprenalin. The maximum achievable effect of the test compound was compared to that of isoprenalin. (The higher the value, the stronger the effect.)

2. From the logarithm of the injected dosages and the effect after injection, the dosage was determined which achieves one-half of the maximum effect (ED 50). The dosage is given in µg/kg. (The lower this value, the more effective is the test substance.)

The values given in the Table below are average values based on two to four individual tests per value.

| | Cardiotonic Effect (in Relation to Isoprenalin) | |
|---|---|---|
| Example No. | $ED_{50}$ (/µ/kg) | dp/dt (%) of 0.3/µg/kg Isoprenalin i.v. |
| 1-(indazol-4-yloxy)-3-[2-(2,6-dimethylphenylamino)-ethylamino]-propan-2-ol. | 2.2 | 87 |
| 1-(indazol-4-yloxy)-3-[2-(3-nitrophenylamino)-ethyl-amino]-propan-2-ol | 2.0 | 66 |
| 1-(indazol-4-yloxy)-3-[3-(2,6-dimethylphenylamino)-propylamino]-propan-3-ol | 4.2 | 110 |
| 1-(indazol-4-yloxy)-3-]2-(indanyl-4-amino)-ethyl-amino]-propan-2-ol | 4.9 | 83 |
| 1-(indol-4-yloxy)-3-[2-(2,6-dimethylphenylamino)-ethylamino]-propan-2-ol | 3.2 | 85 |
| 1-(1-formylindolin-4-yloxy)-3-]2-(2,6-dimethylphenyl-amino)-ethylamino]-propan-2-ol | 4.2 | 87 |
| 1-(benztriazol-4-yloxy)-3-]2-(2,6-dimethylphenylamino)-ethylamino]-propan-2-ol | 3.5 | 100 |

The above data show that the compounds of the invention are outstandingly effective in their cardiotonic action.

The dosage administered depends upon the age, the state of health and the weight of the recipient, the extent of the disease, the nature of other treatments possibly carried out simultaneously, the frequency of the treatment and the nature of the desired action. Usually, the oral daily dosage of the active compound is 0.1 to 200 mg./kg of body weight. Normally, 0.5 to 150 and preferably 1.0 to 100 mg/kg./day in one or more administrations per day are effective for the achievement of the desired results.

It will be understood that the specification and examples are illustrative but not limitative of the present invention and that other embodiments within the spirit and scope of the invention will suggest themselves to those skilled in the art.

What is claimed:

1. Indazoloxypropanolamine of the formula:

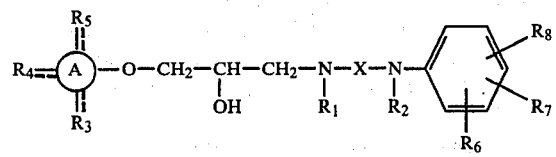

wherein

A is indazole, or partly hydrogenated indazole X is a straight-chained or branched alkylene chain containing 2 to 6 carbon atoms, $R_1$ and $R_2$, which can be the same or different, are hydrogen atoms or lower alkyl or benzyl radicals, $R_3$, $R_4$ and $R_5$, which can be the same or different, are hydrogen atoms or lower alkyl, benzyl, formyl, lower alkanoyl, cyano, hydroxymethyl, lower alkoxycarbonyl or carbamoyl radicals or the divalent substituents sulfur or oxygen and $R_6$, $R_7$ and $R_8$, which can be the same or different, are hydrogen or halogen atoms, lower alkyl, nitro, amino, lower alkylthio or lower alkoxy radicals or $R_6$ and $R_7$ together represent an optionally unsaturated trimethylene chain;

and the pharmacologically acceptable salts thereof.

2. Indazoloxypropanolamine compound as claimed in claim 1, wherein

A is indazole.

3. Indazoloxypropanolamine compound as claimed in claim 1, wherein A is partly hydrogenated.

4. Indazoloxypropanolamine compound as claimed in claim 1, wherein $R_1$ and $R_2$ are both hydrogen.

5. Indazoloxypropanolamine compound as claimed in claim 1, wherein one of $R_1$ and $R_2$ are alkyl.

6. Indazoloxypropanolamine compound as claimed in claim 1, wherein one of $R_1$ and $R_2$ are benzyl.

7. Indazoloxypropanolamine compound as claimed in claim 1, wherein $R_3$, $R_4$, and $R_5$ are all hydrogen.

8. Indazoloxypropanolamine compound as claimed in claim 1, wherein one of $R_3$, $R_4$ and $R_5$ is lower alkyl.

9. Indazoloxypropanolamine compound as claimed in claim 1, wherein one of $R_3$, $R_4$ and $R_5$ is benzyl.

10. Indazoloxypropanolamine compound as claimed in claim 1, wherein one of $R_3$, $R_4$ and $R_5$ is formyl.

11. Indazoloxypropanolamine compound as claimed in claim 1, wherein one of $R_3$, $R_4$ and $R_5$ is lower alkanoyl.

12. Indazoloxypropanolamine compound as claimed in claim 1, wherein one of $R_3$, $R_4$ and $R_5$ is cyano.

13. Indazoloxypropanolamine compound as claimed in claim 1, wherein one of $R_3$, $R_4$ and $R_5$ is hydroxymethyl.

14. Indazoloxypropanolamine compound as claimed in claim 1, wherein one of $R_3$, $R_4$ and $R_5$ is lower alkoxycarbonyl.

15. Indazoloxypropanolamine compound as claimed in claim 1, wherein one of $R_3$, $R_4$ and $R_5$ is carbamoyl.

16. Indazoloxypropanolamine compound as claimed in claim 1, wherein at least one of $R_3$, $R_4$ and $R_5$ is sulfur.

17. Indazoloxypropanolamine compound as claimed in claim 1, wherein at least one of $R_3$, $R_4$ and $R_5$ is oxygen.

18. Indazoloxypropanolamine compound as claimed in claim 1, wherein $R_6$, $R_7$ and $R_8$ are all hydrogen.

19. Indazoloxypropanolamine compound as claimed in claim 1, wherein at least one of $R_6$, $R_7$ and $R_8$ is halogen.

20. Indazoloxypropanolamine compound as claimed in claim 1, wherein at least one of $R_6$, $R_7$ and $R_8$ is lower alkyl.

21. Indazoloxypropanolamine compound as claimed in claim 1, wherein at least one of $R_6$, $R_7$ and $R_8$ is nitro.

22. Indazoloxypropanolamine compound as claimed in claim 1, wherein at least one of $R_6$, $R_7$ and $R_8$ is amino.

23. Indazoloxypropanolamine compound as claimed in claim 1, wherein at least one of $R_6$, $R_7$ and $R_8$ is lower alkylthio.

24. Indazoloxypropanolamine compound as claimed in claim 1, wherein at least one of $R_6$, $R_7$ and $R_8$ is lower alkoxy.

25. Indazoloxypropanolamine compound as claimed in claim 1, wherein $R_6$ and $R_7$ together represent an optionally unsaturated trimethylene chain.

26. Indazoloxypropanolamine compound as claimed in claim 1 designated 1-(indazol-4-yloxy)-3-[2-(2,6-dimethylphenylamino)-ethylamine]-propan-2-ol.

27. Indazoloxypropanolamine compound as claimed in claim 1 designated 1-(indazol-4-yloxy)-3-[2-(3-nitrophenylamino)-ethyl-amino]-propan-2-ol.

28. Indazoloxypropanolamine compound as claimed in claim 1 designated 1-(indazol-4-yloxy)-3-[3-(2,6-dimethylphenylamino)-propylamino]-propan-3-ol.

29. Indazoloxypropanolamine compound as claimed in claim 1 designated 1-(indazol-4-yloxy)-3-[2-(indanyl-4-amino)-ethylamino]-propan-2-ol.

30. Composition for combating those cardiac and circulatory disorders which can be ameliorated by a cardiotonic agent comprising an effective cardiotonic amount of an indazoloxypropanolamine compound as claimed in claim 1, together with a pharmacologically acceptable carrier.

31. Method of combatting those cardiac and circulatory disorders which can be ameliorated by a cardiotonic agent comprising administering to an afflicted subject an effective cardiotonic amount of an indazoloxypropanolamine compound as claimed in claim 1.

32. Method as claimed in claim 28, wherein the compound is at least one of:
1-(indazol-4-yloxy)-3-[2-(2,6-dimethyl-phenylamino)ethylamino]-propan-2-ol;
1-(indazol-4-yloxy)-3-[2-(3-nitrophenylamino)-ethylamino]-propan-2-ol;
1-(indazol-4-yloxy)-3-[3-(2,6-dimethylphenylamino)-propylamino]-propan-3-ol;
1-(indazol-4-yloxy)-3-[2-(indanyl-4-amino)-ethylamino]-propan-2-ol;
or pharmacologically compatible salt thereof.

* * * * *